United States Patent [19]
Nishibe et al.

[11] 4,023,206
[45] May 10, 1977

[54] HUMIDITY SENSOR

[75] Inventors: Atsushi Nishibe, Machida; Yoshitaka Kikuchi, Atsugi, both of Japan

[73] Assignee: Sony Corporation, Tokyo, Japan

[22] Filed: Sept. 25, 1975

[21] Appl. No.: 616,666

[30] Foreign Application Priority Data
Oct. 1, 1974 Japan .................. 49-118366[U]

[52] U.S. Cl. .................. 360/75; 73/336.5; 324/65 P; 360/74; 360/130

[51] Int. Cl.² .................. G11B 21/02; G11B 15/18; G11B 15/60; G01W 1/02

[58] Field of Search .............. 73/336.5; 338/34, 35; 324/65 P; 340/235; 200/DIG. 40, 61.05, 61.06; 360/74, 75, 130

[56] References Cited
UNITED STATES PATENTS

| | | | |
|---|---|---|---|
| 2,735,907 | 2/1956 | Inman | 324/65 P |
| 2,937,524 | 5/1960 | Gregor | 324/65 P |
| 2,976,188 | 3/1961 | Kohl | 73/336.5 |
| 3,696,360 | 10/1972 | Gajewski | 73/336.5 |

*Primary Examiner*—Robert S. Tupper
*Attorney, Agent, or Firm*—Lewis H. Eslinger; Alvin Sinderbrand

[57] ABSTRACT

A humidity sensor is formed by a pair of electrodes fitted on the surface of a flexible insulator film such as a polyester film, the pair of electrodes being arranged adjacent to one another with a suitable gap therebetween. Within the gap between the adjacent electrodes, a rough surface portion is formed on the insulator and/or the electrodes so that condensed dewdrops on the gap are automatically dispersed, and accordingly the sensitivity of the humidity sensor is improved.

A video tape recording and/or reproducing apparatus is also disclosed which employs the humidity sensor described above. In this case, the humidity sensor is mounted on the tape guide drum of the video tape recording and/or reproducing apparatus for detecting the humidity thereon.

2 Claims, 6 Drawing Figures

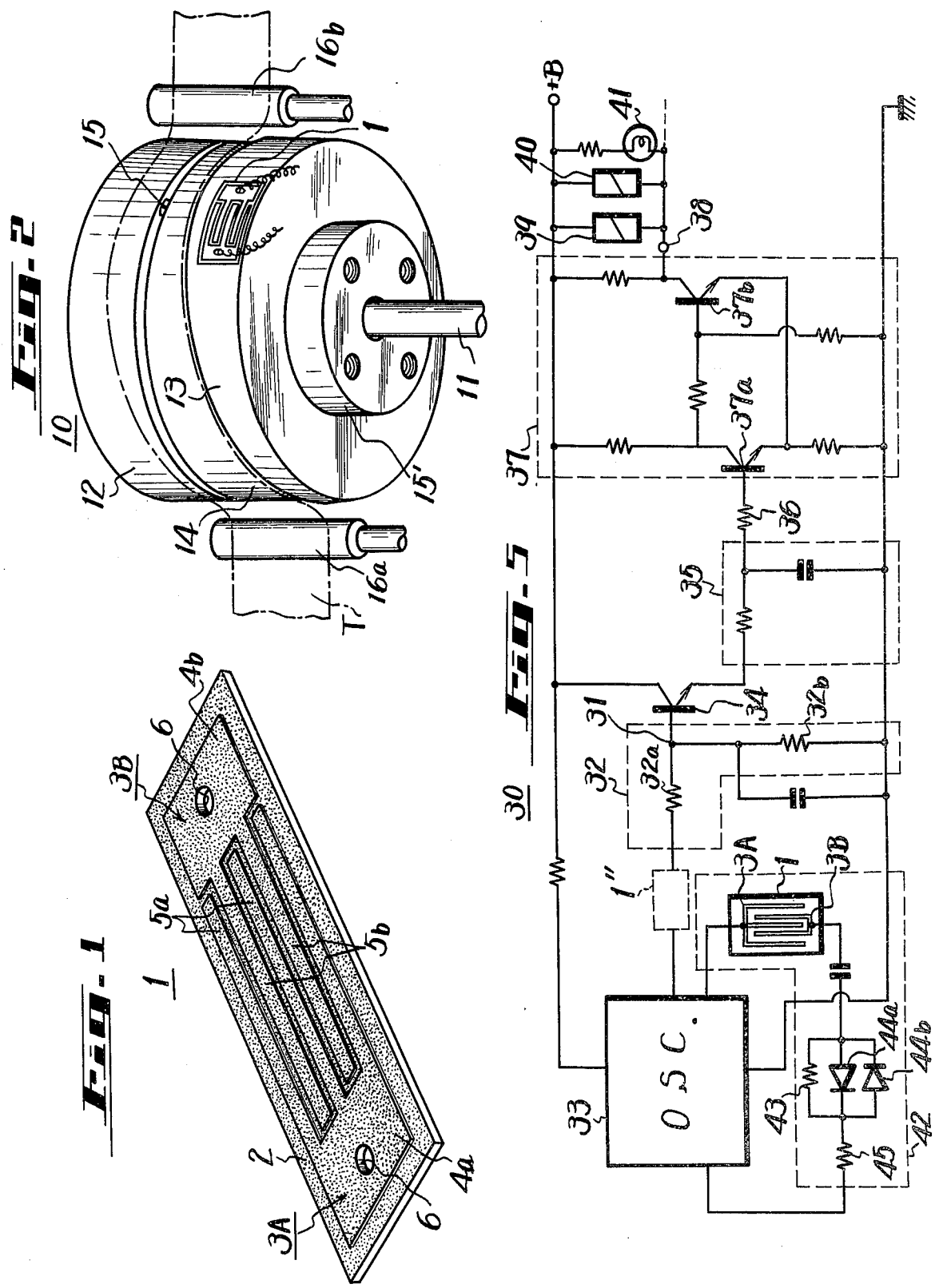

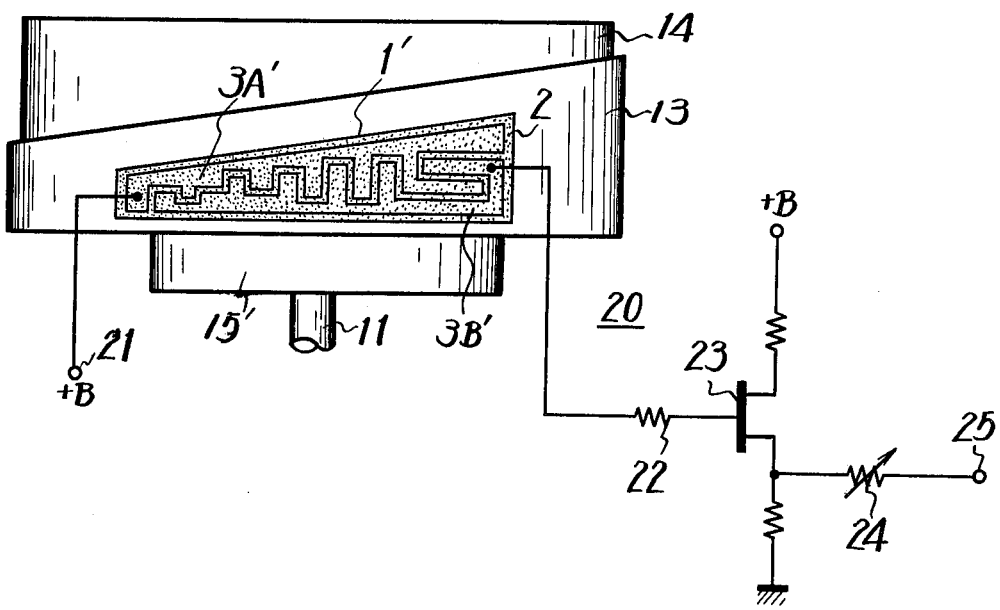
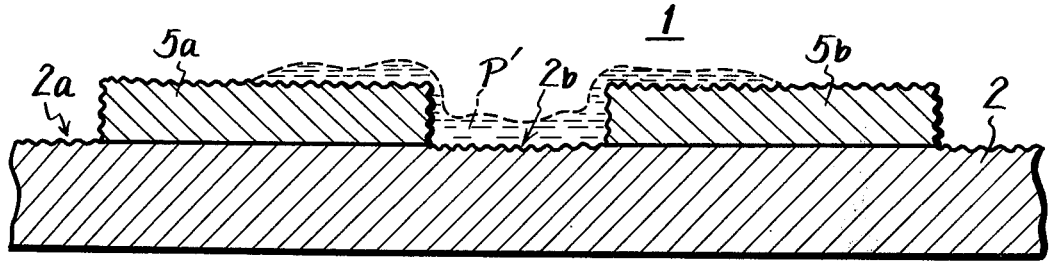
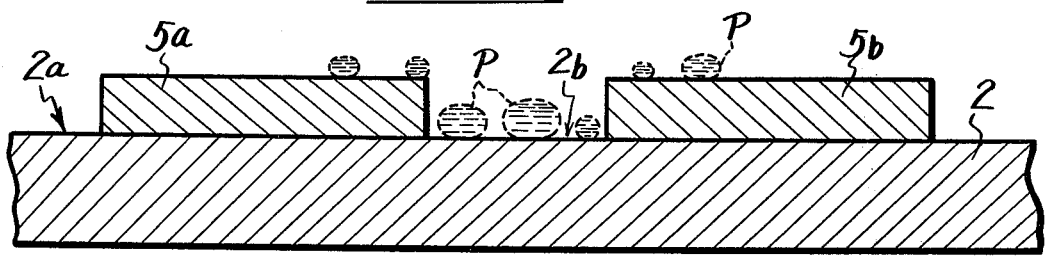

HUMIDITY SENSOR

BACKGROUND OF THE INVENTION

1. Field of the Invention

This invention relates generally to a novel humidity sensor having a flexible insulator film with two electrodes thereon.

This invention is directed more particularly to a humidity sensor which detects a dew precipitated thereon in an ambient atmosphere at the dew point and which is suitable for detecting humidity at the main parts of electronic instruments such as the tape guide portion of a VTR which dislike the formation of dew-drops or detecting the appearance of dewdrops on the window glass of vehicles.

This invention is directed also to a video tape recording and/or reproducing apparatus employing the humidity sensor mentioned as above.

2. Description of the Prior Art

In a magnetic recording and/or reproducing apparatus having a guide means for guiding a recording medium such as a magnetic tape by winding the magnetic tape on the guide means, if its ambient temperature is varied, dewdrops are precipitated on the surface of the guide means. When the dewdrops are formed on the surface of the guide means, the magnetic tape adheres to the surface of the guide means, which results in that the tape can not travel normally. Further, due to the dewdrop or humidity on the surface of the guide means, the tape itself is deformed frequently and hence undesired phenomena such as so-called jitters and skews are apt to be caused.

In the art, there has been proposed a humidity sensor having a resistor, whose resistance value is changed in accordance with the state of dewdrops appeared thereon, fitted on the surface of the tape guide member for detecting the state of dewdrops as a variation of the resistance value of the resistor.

One of practical examples of the prior art humidity sensor has a dew detecting element on the peripheral surface of a helical guide of a tape guide drum for deriving the humidity of whole the drum as a variation of electric resistance value and a level detecting circuit including the detecting element an output signal from which is used to control the operation system of a VTR suitably.

With such a prior art humidity sensor, when dewdrops appear on the tape guide drum, tape guide members and the like, the above undesired phenomena can be avoided by some extents. However, the sensitivity or response of the dew detecting element to the humidity of the prior art is a problem. The reason why the resistance between a pair of electrodes is varied by humidity is that the pair of electrodes are bridged by the dewdrops. In practice, however, even when fine particles of dewdrops appear between the electrodes, there is the case that no output signal is fed from the output terminals of the humidity sensor to the following stage of an amplifier.

SUMMARY OF THE INVENTION

The present invention has its base on the discovery or ascertainment that there are many cases where the above defect of the prior art is caused by the fact that the dewdrop formed on the surface of dew detecting element are divided into fine independent condensed particles by the surface tension thereof between the electrodes and accordingly the electrodes are not bridged by the fine condensed dewdrops.

Accordingly, an object of the present invention is to provide a humidity sensor which has a novel dew detecting element or sensor element to improve and enhance the detecting sensitivity of the humidity sensor.

Another object of the invention is to provide a video tape recording and/or reproducing apparatus employing the above humidity sensor which is mounted on its tape guide drum for detecting the humidity thereon.

According to an aspect of the invention, there is provided a humidity sensor which comprises a humidity sensor member formed of a pair of electrodes made of stainless steel or the like and mounted in opposed relation with each other on an insulator film made of, for example, polyester system with a suitable gap. In this case, the surface of the insulator on the gap between the electrodes is made rough or coarse, so that condensed dewdrops formed on the humidity sensor are dispersed uniformly over the surface thereof to enhance the detecting sensitivity thereof.

According to another aspect of the invention, there is proposed a video tape recording and/or reproducing apparatus which employs the humidity sensor mentioned just above on its tape guide drum for detecting the humidity thereon.

The other objects, features and advantages of the invention will become apparent from the following description taken in conjunction with the accompanying drawings.

BRIEF DESCRIPTION OF THE DRAWINGS

FIG. 1 is a perspective view showing an embodiment of the humidity sensor according to this invention;

FIG. 2 is a perspective view showing an example of the tape guide drum on which the humidity sensor according to the invention is mounted;

FIG. 3 is a schematic diagram showing a humidity detecting circuit using another example of the humidity sensor of the invention which is applied to a VTR;

FIGS. 4A and 4B are enlarged cross-sectional views for explaining the formation of dewdrops on humidity sensors; and FIG. 5 is a connection diagram including the humidity sensor of the invention applied to a VTR.

DESCRIPTION OF THE PREFERRED EMBODIMENT

An embodiment of the humidity sensor according to the present invention will be now described with reference to FIG. 1.

In FIG. 1, reference numeral 1 generally designates the humidity sensor of the invention and 2 an insulator base plate of a rectangular shape which is a flexible film made of resin such as Mylar (Trade Name). A pair of electrodes 3A and 3B, which are made of stainless steel or the like, are formed on one surface of the flexible insulator film 2 by a well-known etching method. In the illustrated example, the electrodes 3A and 3B have connection portions 4a and 4b at the ends near the longitudinal ends of the flexible insulator film 2 for connection to external lead wires, respectively. The electrode 3A has three sensor elements or members 5a of band shape extended from the connection portion 4a, while the other electrode 3B has two sensor elements or members 5b of band shape extended from the connection portion 4b. As shown in FIG. 1, both the sensor elements 5a and 5b are arranged on the insulator film 2 along its longitudinal direction alternately. In this case, there are formed uniform and predetermined width of gaps between the adjacent sensor elements 5a and 5b and between the free ends of the respective sensor elements 5a, 5b and the end edges of the connection portions 4b, 4a opposing the former. Throughout the connection portions 4a and 4b and the insulator film 2 therebeneath, there are formed throughout bores 6 which serve for the humidity sensor 1 to be attached to an object whose humidity is detected, for example, a helical guide 13 of a tape guide drum 10 (refer to FIG. 2) and also serve to connect lead wires to the electrodes 3A and 3B, respectively.

FIG. 2 shows the tape guide drum 10 which has an upper rotary drum 12 on a shaft 11, a lower fixed drum 14 on the shaft 11 and two rotary magnetic heads 15 with an angular distance of 180° in the gap between the drums 12 and 14(in FIG. 2, only one magnetic head 15 is shown). A magnetic tape T is helically guided on the peripheral surfaces of the drums 12 and 14 to record (or reproduce) a video signal of two field-one frame thereon (or therefrom). On the peripheral surface of the lower guide drum 14, there is formed the helical guide 13. A boss 15' is provided around the shaft 11 for fixing the lower drum 14. The tape guide drum 10 described above is well known. In FIG. 2, reference numerals 16a and 16b designate guide pins which act to restrict the angle of the tape T to the peripheral surface of the guide drum 10. The humidity sensor 1 shown in FIG. 1 is mounted on the peripheral surface of the lower drum 14 in this example.

FIG. 3 shows an example of the humidity detecting circuit 20 of the invention in simplest form. In this example, a humidity sensor 1' which is different from the humidity sensor 1 shown in FIG. 1 in shape or configuration is used. That is, electrodes 3A' and 3B' and insulator film 2 are different from those shown in FIG. 1 in shape or configuration, but the gap between the electrodes 3A' and 3B' is substantially same as that shown in FIG. 1 in width and operation. One of the electrodes or electrode 3A' in the illustrated example is supplied with a certain value of DC voltage +B from a power or voltage source terminal 21, while the other electrode 3B' is connected through a resistor 22 to, for example, the gate electrode of an FET 23 which has a high input impedance characteristic. An output terminal 25 is led out from the source (or drain) electrode of the FET 23 through a variable resistor 24. An output signal obtained at the output terminal 25 is in proportion to the amount of dewdrops precipitated on the surface of the humidity sensor 1', so that the output signal is used to detect the humidity after being amplified. The variable resistor 24 is used to adjust the detecting sensitivity of the circuit 20.

According to the present invention, the printed surface including the electrodes 3A and 3B(3A' and 3B') or at least the surface of the insulator film 2 of the humidity sensor 1,(1') are made rough or coarse to lower the surface tension of dewdrops precipitated thereon and hence to help the bridging effect of dewdrops between the electrodes 3A and 3B(3A' and 3B'). Thus, the humidity detecting sensitivity of the humidity sensor 1(1') is increased much, which will be now described with reference to FIGS. 4A and 4B.

FIG. 4A is a partial cross-sectional and enlarged view on the line I — I' in FIG. 1. For the sake of better understanding, the case where the surface 2a of the insulator film 2 and the surfaces of the electrodes or sensor elements 5a and 5b are not made rough will be firstly described with reference to FIG. 4B showing the prior art humidity sensor similar in form to FIG. 4A. As shown in FIG. 4B, when dewdrops P are precipitated on the surfaces of the sensor elements 5a and 5b and the surface of the insulator film 2 between the sensor elements 5a and 5b(gap), the dewdrops P become approximately spheres due to the surface tension thereof as well known. Thus, these dewdrops P remain independent respectively, until their number arrives at a critical value. Therefore, the sensor elements 5a and 5b can not be bridged by the dewdrops P which are not arrived at the critical value as shown in FIG. 4B, namely the resistance between the electrodes 3A and 3B is not varied by the dewdrops P at this state. Thus, even if dewdrops appear but they are in the state shown in FIG. 4B, the humidity can not be detected by such a humidity sensor shown in FIG. 4B.

According to the present invention, as shown in FIG. 4A, a surface 2a of the insulator film 2 including a gap surface 2b between the sensor elements 5a and 5b and the surfaces of the sensor elements 5a and 5b of the humidity sensor 1 are all made rough with a suitable degree, so that when dewdrops such as shown in FIG. 4B are precipitated on the rough surfaces of the humidity sensor 1 according to the invention, their surface tensions are lowered by the rough surfaces and hence they can not remain as independent spheres as in the case where the dewdrops are precipitated on the flat and smooth surface as in the case of FIG. 4B. As a result, the dewdrops are irregularly expanded on the rough surfaces and become a bridging water P' as shown in FIG. 4A. Thus, the resistance value between the sensor elements 5a and 5b and accordingly the resistance value between the electrodes 3A and 3B is varied even if the dewdrops are small in amount.

Therefore, the humidity on an object to be detected, for example, tape guide drum 10 shown in FIG. 2 can be detected with high sensitivity. That is, an electric signal in response to the humidity on the tape guide drum 10 can be derived at the output terminal 25 of the detecting circuit 20 shown in FIG. 3 even though the humidity is rather low.

The surface of the humidity sensor 1 of the present invention can be roughened by the sand-blast method or other chemical treatments.

In the example shown in FIG. 4A, all the free or upper surface of the humidity sensor 1 is made rough, but it may be possible that only the free or upper surface of the insulator film 2 between the sensor elements 5a and 5b is roughened with the same effect.

In the above description, the surface of the insulator film 2 on the gap between the two sensor elements 5a and 5b is roughened, but it is also possible with the same effect that the surface on the gap is made smooth but the surfaces of the two sensor elements 5a and 5b are made rough. In this case, a stainless steel foil is coated on the insulator film 2 such as a polyester film, the surface of the foil is made rough by, for example, electrolysis or the like and then made to have the electrode pattern mentioned previously by the photoetching method as an ordinary semiconductor manufacturing method.

It is a preferred surface roughness that the maximum peak-to-peak hight of the roughened hill and dent portion is larger than $0.8\beta$.

If a DC current flows through the detecting resistor or the electrodes 3A and 3B of the humidity sensor 1 for a long period of time, they are apt to be oxidized with the help of dewdrops and then corroded finally. Thus, they become useless.

FIG. 5 shows a circuit diagram using the humidity sensor 1 of the invention with which the life time span of the humidity sensor 1 is prolonged and hence it can be used for a long period of time. In this case, the humidity sensor 1 is applied to a VTR, practically.

In FIG. 5, reference numeral 30 generally designates the humidity detecting circuit using on its tape guide drum 10 (not shown in FIG. 10) the humidity sensor 1 which is inserted in to the feedback circuit of an oscillator circuit 33, and 32 a voltage divider circuit consisting of resistors 32a and 32b. When the oscillator 33 is an astable multivibrator, it generates a rectangular waveform signal. The rectangular waveform signal from the oscillator 33 is supplied to the voltage divider 32. A rectangular waveform voltage obtained at the connection point 31 between the resistors 32a and 33a is supplied through the base-emitter path of a transistor 34 to a peak hold circuit 35 to be a DC voltage. This DC voltage from the peak hold circuit 35 is supplied through a resistor 36 to a level detecting circuit such as a Schmidt trigger circuit 37 which includes a transistor 37a at the input side thereof and a transistor 37b at the output side thereof. Thus, a detected signal is obtained at an output terminal 38 led out from the collector electrode of the transistor 37b. In this example, the humidity sensor 1 is inserted into the feedback circuit 42 of the oscillator 33, as described above.

With the detecting circuit 30, when no dewdrop is formed on the surface of the tape guide drum 10 (not shown in FIG. 5) and hence no dewdrop appears on the humidity sensor 1, the resistance value of the humidity sensor 1 is large. Thus, the feeding back amount of the oscillator 33 is small, and accordingly the rectangular voltage appearing at the connection point 31 is low. Accordingly, the output voltage obtained from the peak hold circuit 35 is low. Therefore, the input side transistor 37a of the Schmidt trigger circuit 37 is OFF and its output side transistor 37b is ON. Thus, an output signal appearing at the output terminal 38 is 0.

When dewdrops are precipitated on the surface of the guide drum 10, dewdrops are also formed on the humidity sensor 1 to lower its resistance value. Thus, the feeding back amount to the oscillator 33 increases and hence the rectangular voltage obtained at the connection point 31 of the voltage divider circuit 32 becomes high. Accordingly, the output voltage from the peak hold circuit 35 becomes high to exceed the Schmidt level of the Schmidt trigger circuit 37. Thus, its transistor 37a becomes ON but its transistor 37b becomes OFF to produce the output signal of 1 at the output terminal 38.

In the example shown in FIG. 5, a relay 39 associated with the power source circuit to the motor for driving the tape (not shown in FIG. 5), a relay 40 associated with the power source circuit to the motor for driving the head drum, and a lamp 41 are connected to the output terminal 38, so that when the output signal produced at the output terminal 38 is 1 which indicates the appearance of dewdrops on the guide drum 10, the power source circuit to the tape driving motor is opened by the relay 39, the power source circuit to the head driving motor is opened by the relay 40 to stop the recording and reproducing apparatus or the lamp 41 is lit for alarming the appearance of dewdrops.

As may be apparent from the above description, with the detecting circuit of the present invention, the signal supplied to the humidity sensor 1 is such a signal that has a predetermined period and hence the current flows through the humidity sensor 1 intermittently, so that the electrodes 3A and 3B of the humidity sensor 1 according to the invention are not corroded easily as compared with the case that the DC current passes through the humidity sensor 1.

When a rectangular waveform signal with the duty factor of 20% is supplied to the humidity sensor 1, its life time span can be elongated by five times as compared with the case that the DC circuit is supplied to the humidity sensor 1.

The resistance value of the humidity sensor 1 is varied little at a remarkably short period, but when the Schmidt trigger circuit 37 is employed as the level detecting circuit as shown in FIG. 5, it is avoided that the output signal is changed alternately between 1 and 0.

As shown in FIG. 5, a circuit consisting of a parallel circuit formed of a resistor 43 and diodes 44a, 44b, which are connected in opposite polarities, and a resistor 44 is inserted into the positive feedback loop 42 of the oscillator 33, if necessary. Thus, before the start of oscillation the gain of the oscillator 33 is low, the feedback voltage is small and hence the diodes 44a, 44b are OFF, while after the start of oscillation the diodes 44a, 44b become ON, the resistor 43 is neglected and only the resistor 45 is inserted into the feedback circuit 42 to increase the feedback amount. Thus, the so-called hysteresis characteristics of the oscillator 33 can be obtained by the resistance of the resistor 43. That is, the resistance value of the humidity sensor 1 is different at the start and stop of the oscillation of the oscillator 33, and hence a small amount of the resistance variation of the humidity sensor 1 does not affect the output. Thus, a stable output can be obtained.

Even if the humidity sensor is inserted between the output terminal of the oscillator 33 and the voltage divider 32 as shown by a dotted line block 1" in FIG. 5, the same effect can be performed.

If the surface of the humidity sensor 1 is swept by a brush on the like at every loading of the tape on the guide drum 10, the dewdrops can be distributed wide further over the surface of the humidity sensor 1.

The above description is given mainly on the case that the humidity sensor according to the present invention is mounted on the tape guide drum of a VTR, but it may be apparent that the above case is a mere example and that the humidity sensor of the invention is applied to the tape guide member of similar tape recorders, to the main parts of various electronic instruments which are desired to be free from humidity, and to the glasses of moving vehicles for detecting dewdrops thereon with good results.

Further, it will be understood that a device which dries dewdrops automatically may be operated by the humidity sensor of the invention or only an alarm is raised by using the humidity sensor of the invention when dewdrops appear.

It will be understood that various modifications and changes could be made by one skilled in the art without departing from the spirits or scope of the novel concepts of the present invention.

We claim as our invention:

1. A video tape recording and/or reproducing apparatus comprising:

a tape guide drum around which a tape is guided and including rotary head means for scanning the tape guided on the drum as the tape is longitudinally driven;

tape drive means for driving the tape around the guide drum;

a humidity sensor including an insulating film adhered to said tape guide drum, and a pair of electrodes arranged adjacent to each other on a surface of said insulating film with a gap between said electrodes for providing a resistance therebetween which varies generally inversely in respect to the degree of humidity in the ambient atmosphere; and circuit means connected with said sensor for sensing said resistance halting the rotation of said head means and the driving of said tape when said resistance falls below a predetermined value.

2. A video tape recording and/or reproducing apparatus according to claim 1; in which said circuit means includes an oscillator for providing an intermittent output, a peak-hold circuit for providing a DC voltage proportional to the level of said intermittent output of the oscillator, means connecting said sensor with said oscillator so as to receive said intermittent output and to vary said level of the intermittent output, as received by said peak-hold circuit, substantially in accordance with said resistance of the sensor, and level detecting means for detecting the level of said DC voltage and for halting said rotation of the head means and said driving of the tape in dependence on the detected DC voltage level.

* * * * *